US012558154B2

(12) United States Patent
Govari et al.

(10) Patent No.: US 12,558,154 B2
(45) Date of Patent: Feb. 24, 2026

(54) BALLOON CATHETER HAVING ABLATION AND RETURN ELECTRODES

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 502 days.

(21) Appl. No.: 16/994,428

(22) Filed: Aug. 14, 2020

(65) Prior Publication Data

US 2022/0047327 A1 Feb. 17, 2022

(51) Int. Cl.
| | |
|---|---|
| *A61B 18/14* | (2006.01) |
| *A61B 18/12* | (2006.01) |
| *A61B 18/00* | (2006.01) |

(52) U.S. Cl.
CPC ...... *A61B 18/1492* (2013.01); *A61B 18/1206* (2013.01); *A61B 2018/0022* (2013.01);
(Continued)

(58) Field of Classification Search
CPC ............ A61B 18/1492; A61B 18/1206; A61B 2018/0022; A61B 2018/00267; A61B 2018/00577; A61B 2018/1253
See application file for complete search history.

(56) References Cited

U.S. PATENT DOCUMENTS

| | | | |
|---|---|---|---|
| D123,782 S | 12/1940 | Paul | |
| 3,316,896 A | 5/1967 | Louis | |
| (Continued) | | | |

FOREIGN PATENT DOCUMENTS

| | | |
|---|---|---|
| CN | 101422637 A | 5/2009 |
| CN | 102271607 A | 12/2011 |
| (Continued) | | |

OTHER PUBLICATIONS

Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.

(Continued)

*Primary Examiner* — Eun Hwa Kim
*Assistant Examiner* — Catherine Premraj

(57) ABSTRACT

A catheter includes an expandable frame for insertion into an organ of a patient, one or more first electrodes, and a second electrode. The one or more first electrodes are disposed on the expandable frame at one or more first positions for placing in contact with a target tissue of the organ, and are configured to perform one or both of: (i) sensing one or more electrical signals from the target tissue, and (ii) applying one or more ablation pulses to the target tissue. The second electrode is disposed within an internal volume of the expandable frame, at a second position that is not in contact with the target tissue while the one or more first electrodes contact the target tissue, and is configured to serve as a return or common electrode for the electrical signals.

17 Claims, 2 Drawing Sheets

(52) U.S. Cl.
CPC .............. *A61B 2018/00267* (2013.01); *A61B 2018/00577* (2013.01); *A61B 2018/1253* (2013.01)

(56) References Cited

U.S. PATENT DOCUMENTS

| | | | |
|---|---|---|---|
| 4,276,874 A | 7/1981 | Wolvek et al. |
| 4,587,975 A | 5/1986 | Salo et al. |
| 4,709,698 A | 12/1987 | Johnston et al. |
| 4,805,621 A | 2/1989 | Heinze et al. |
| 5,178,957 A | 1/1993 | Kolpe et al. |
| 5,391,199 A | 2/1995 | Ben-Haim |
| 5,429,617 A | 7/1995 | Hammersmark et al. |
| 5,582,609 A | 12/1996 | Swanson et al. |
| 5,584,830 A | 12/1996 | Ladd et al. |
| 5,702,386 A | 12/1997 | Stern et al. |
| 5,718,241 A | 2/1998 | Ben-Haim et al. |
| 5,797,903 A | 8/1998 | Swanson et al. |
| 5,860,974 A | 1/1999 | Abele |
| 5,971,983 A | 10/1999 | Lesh |
| 6,012,457 A | 1/2000 | Lesh |
| 6,024,740 A | 2/2000 | Lesh et al. |
| 6,042,580 A | 3/2000 | Simpson |
| 6,123,718 A | 9/2000 | Tu et al. |
| 6,142,993 A | 11/2000 | Whayne et al. |
| 6,164,283 A | 12/2000 | Lesh |
| 6,171,275 B1 | 1/2001 | Webster, Jr. |
| 6,176,832 B1 | 1/2001 | Habu et al. |
| 6,198,974 B1 | 3/2001 | Webster, Jr. |
| 6,226,542 B1 | 5/2001 | Reisfeld |
| 6,239,724 B1 | 5/2001 | Doron et al. |
| 6,301,496 B1 | 10/2001 | Reisfeld |
| 6,322,558 B1 | 11/2001 | Taylor et al. |
| 6,332,089 B1 | 12/2001 | Acker et al. |
| 6,380,957 B1 | 4/2002 | Banning |
| 6,402,740 B1 | 6/2002 | Ellis et al. |
| D462,389 S | 9/2002 | Provence et al. |
| 6,471,693 B1 | 10/2002 | Carroll et al. |
| 6,484,118 B1 | 11/2002 | Govari |
| 6,522,930 B1 | 2/2003 | Schaer et al. |
| 6,618,612 B1 | 9/2003 | Acker et al. |
| 6,656,174 B1 | 12/2003 | Hegde et al. |
| 6,690,963 B2 | 2/2004 | Ben-Haim et al. |
| 6,814,733 B2 | 11/2004 | Schwartz et al. |
| 6,892,091 B1 | 5/2005 | Ben-Haim et al. |
| 6,893,433 B2 | 5/2005 | Lentz |
| 6,986,744 B1 | 1/2006 | Krivitski |
| 6,987,995 B2 | 1/2006 | Drysen |
| 6,997,924 B2 | 2/2006 | Schwartz et al. |
| 7,142,903 B2 | 11/2006 | Rodriguez et al. |
| 7,156,816 B2 | 1/2007 | Schwartz et al. |
| 7,274,957 B2 | 9/2007 | Drysen |
| 7,340,307 B2 | 3/2008 | Maguire et al. |
| 7,377,906 B2 | 5/2008 | Selkee |
| 7,442,190 B2 | 10/2008 | Abbound et al. |
| 7,536,218 B2 | 5/2009 | Govari et al. |
| 7,591,799 B2 | 9/2009 | Selkee |
| 7,593,760 B2 | 9/2009 | Rodriguez et al. |
| 7,720,517 B2 | 5/2010 | Drysen |
| 7,756,576 B2 | 7/2010 | Levin |
| 7,842,031 B2 | 11/2010 | Abboud et al. |
| 7,853,302 B2 | 12/2010 | Rodriguez et al. |
| 8,000,765 B2 | 8/2011 | Rodriguez et al. |
| 8,021,327 B2 | 9/2011 | Selkee |
| 8,048,032 B2 | 11/2011 | Root et al. |
| 8,231,617 B2 | 7/2012 | Satake |
| 8,267,932 B2 | 9/2012 | Baxter et al. |
| 8,275,440 B2 | 9/2012 | Rodriguez et al. |
| 8,348,888 B2 | 1/2013 | Selkee |
| 8,357,152 B2 | 1/2013 | Govari et al. |
| D682,289 S | 5/2013 | DiJulio et al. |
| D682,291 S | 5/2013 | Baek et al. |
| 8,456,182 B2 | 6/2013 | Bar-Tal et al. |
| D690,318 S | 9/2013 | Kluttz et al. |
| D694,652 S | 12/2013 | Tompkin |
| 8,641,709 B2 | 2/2014 | Sauvageau et al. |
| 8,721,590 B2 | 5/2014 | Seward et al. |
| 8,777,161 B2 | 7/2014 | Pollock et al. |
| D716,340 S | 10/2014 | Bresin et al. |
| 8,852,181 B2 | 10/2014 | Malecki et al. |
| D720,766 S | 1/2015 | Mandal et al. |
| D721,379 S | 1/2015 | Moon et al. |
| D724,618 S | 3/2015 | Shin |
| 8,998,893 B2 | 4/2015 | Avitall |
| D729,263 S | 5/2015 | Ahn et al. |
| 9,060,756 B2 | 6/2015 | Bencini et al. |
| 9,089,350 B2 | 7/2015 | Willard |
| D736,780 S | 8/2015 | Wang |
| 9,126,023 B1 | 9/2015 | Sahatjian et al. |
| D740,308 S | 10/2015 | Kim et al. |
| D743,424 S | 11/2015 | Danielyan et al. |
| D744,000 S | 11/2015 | Villamor et al. |
| 9,173,758 B2 | 11/2015 | Brister et al. |
| D747,742 S | 1/2016 | Fan et al. |
| D750,644 S | 3/2016 | Bhutani et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,320,631 B2 | 4/2016 | Moore et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| 9,474,486 B2 | 10/2016 | Eliason et al. |
| D783,037 S | 4/2017 | Hariharan et al. |
| 9,655,677 B2 | 5/2017 | Salahieh et al. |
| D791,805 S | 7/2017 | Segars |
| 9,757,180 B2 | 9/2017 | Gelfand et al. |
| 9,795,442 B2 | 10/2017 | Salahieh et al. |
| 9,907,610 B2 | 3/2018 | Beeckler et al. |
| 9,925,001 B2 | 3/2018 | Willard et al. |
| 9,956,035 B2 | 5/2018 | Govari et al. |
| 10,342,608 B2 | 7/2019 | Wang et al. |
| 10,362,952 B2 | 7/2019 | Basu et al. |
| 10,413,356 B2 | 9/2019 | Stone et al. |
| D861,717 S | 10/2019 | Brekke et al. |
| 10,517,621 B1 | 12/2019 | Hakala et al. |
| 10,688,278 B2 | 6/2020 | Beeckler et al. |
| 10,751,534 B2 | 8/2020 | Hiller et al. |
| 10,799,281 B2 | 10/2020 | Goertzen et al. |
| 2001/0031961 A1 | 10/2001 | Hooven |
| 2002/0002369 A1 | 1/2002 | Hood |
| 2002/0006455 A1 | 1/2002 | Levine |
| 2002/0065455 A1 | 5/2002 | Ben-Haim et al. |
| 2002/0068931 A1 | 6/2002 | Wong et al. |
| 2002/0077627 A1 | 6/2002 | Johnson et al. |
| 2002/0160134 A1 | 10/2002 | Ogushi et al. |
| 2003/0018327 A1 | 1/2003 | Truckai et al. |
| 2003/0028183 A1 | 2/2003 | Sanchez et al. |
| 2003/0050637 A1 | 3/2003 | Maguire et al. |
| 2003/0060820 A1 | 3/2003 | Maguire et al. |
| 2003/0120150 A1 | 6/2003 | Govari |
| 2003/0144658 A1 | 7/2003 | Schwartz et al. |
| 2004/0068178 A1 | 4/2004 | Govari |
| 2004/0122445 A1 | 6/2004 | Butler et al. |
| 2004/0147920 A1 | 7/2004 | Keidar |
| 2004/0225285 A1 | 11/2004 | Gibson |
| 2005/0070887 A1 | 3/2005 | Taimisto et al. |
| 2005/0096647 A1 | 5/2005 | Steinke et al. |
| 2005/0119686 A1 | 6/2005 | Clubb |
| 2006/0013595 A1 | 1/2006 | Trezza et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0287994 A1 | 12/2007 | Patel |
| 2008/0018891 A1 | 1/2008 | Hell et al. |
| 2008/0021313 A1 | 1/2008 | Eidenschink et al. |
| 2008/0051707 A1 | 2/2008 | Phan et al. |
| 2008/0140072 A1 | 6/2008 | Stangenes et al. |

(56) References Cited

U.S. PATENT DOCUMENTS

| | | |
|---|---|---|
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0249463 A1 | 10/2008 | Pappone et al. |
| 2008/0262489 A1 | 10/2008 | Steinke |
| 2008/0281312 A1 | 11/2008 | Werneth et al. |
| 2009/0093806 A1 | 4/2009 | Govari et al. |
| 2009/0163890 A1 | 6/2009 | Clifford et al. |
| 2009/0182318 A1 | 7/2009 | Abboud et al. |
| 2009/0259274 A1* | 10/2009 | Simon ................. A61N 1/0517 |
| | | 607/42 |
| 2009/0270850 A1 | 10/2009 | Zhou et al. |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0130648 A1 | 6/2011 | Beeckler et al. |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0136350 A1 | 5/2012 | Goshgarian et al. |
| 2012/0143177 A1 | 6/2012 | Avitall |
| 2012/0143293 A1 | 6/2012 | Mauch et al. |
| 2012/0191079 A1 | 7/2012 | Moll et al. |
| 2012/0209260 A1 | 8/2012 | Lambert et al. |
| 2012/0271140 A1 | 10/2012 | Kordis et al. |
| 2012/0296232 A1 | 11/2012 | Ng |
| 2013/0085360 A1 | 4/2013 | Grunewald |
| 2013/0085493 A1 | 4/2013 | Bloom et al. |
| 2013/0090649 A1 | 4/2013 | Smith et al. |
| 2013/0090651 A1 | 4/2013 | Smith |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0197499 A1 | 8/2013 | Lalonde et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0031810 A1 | 1/2014 | Mahvi et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | DeBoer et al. |
| 2014/0243821 A1 | 8/2014 | Salahieh et al. |
| 2014/0275993 A1 | 9/2014 | Ballakur |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1 | 12/2014 | Salahieh et al. |
| 2015/0005799 A1 | 1/2015 | Lindquist et al. |
| 2015/0025532 A1* | 1/2015 | Hanson .............. A61B 18/1492 |
| | | 156/60 |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0141798 A1 | 5/2015 | Bar-Tal |
| 2015/0141982 A1 | 5/2015 | Lee |
| 2015/0157382 A1 | 6/2015 | Avitall et al. |
| 2015/0196740 A1 | 7/2015 | Mallin et al. |
| 2015/0216591 A1 | 8/2015 | Cao et al. |
| 2015/0216650 A1 | 8/2015 | Shaltis |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0327805 A1 | 11/2015 | Ben-Haim |
| 2015/0341752 A1 | 11/2015 | Flynn |
| 2015/0351836 A1 | 12/2015 | Prutchi |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0196635 A1 | 7/2016 | Cho et al. |
| 2016/0199127 A1 | 7/2016 | Prutchi |
| 2016/0256305 A1 | 9/2016 | Longo et al. |
| 2016/0374748 A9 | 12/2016 | Salahieh et al. |
| 2017/0007157 A1 | 1/2017 | Gross et al. |
| 2017/0007158 A1* | 1/2017 | Gross ................... A61B 5/7475 |
| 2017/0042614 A1 | 2/2017 | Salahieh et al. |
| 2017/0042615 A1* | 2/2017 | Salahieh .................. A61B 5/01 |
| 2017/0080192 A1 | 3/2017 | Giasolli et al. |
| 2017/0143359 A1 | 5/2017 | Nguyen et al. |
| 2017/0164464 A1 | 6/2017 | Weinkam et al. |
| 2017/0311829 A1 | 11/2017 | Beeckler et al. |
| 2017/0311893 A1 | 11/2017 | Beeckler et al. |
| 2017/0312012 A1 | 11/2017 | Harlev et al. |
| 2017/0312022 A1 | 11/2017 | Beeckler et al. |
| 2017/0312420 A1* | 11/2017 | Harlev .............. A61B 18/1492 |
| 2017/0347896 A1 | 12/2017 | Keyes et al. |
| 2017/0348049 A1 | 12/2017 | Vrba et al. |
| 2018/0042674 A1 | 2/2018 | Mickelsen |
| 2018/0074693 A1 | 3/2018 | Jones et al. |
| 2018/0110562 A1 | 4/2018 | Govari et al. |
| 2018/0125575 A1 | 5/2018 | Schwartz et al. |
| 2018/0161093 A1 | 6/2018 | Basu et al. |
| 2018/0184982 A1* | 7/2018 | Basu ................... A61B 5/6858 |
| 2018/0256247 A1 | 9/2018 | Govari et al. |
| 2018/0280080 A1 | 10/2018 | Govari et al. |
| 2018/0333162 A1 | 11/2018 | Saab |
| 2018/0344187 A1 | 12/2018 | Osadchy et al. |
| 2018/0368927 A1 | 12/2018 | Lyons et al. |
| 2019/0059818 A1 | 2/2019 | Herrera et al. |
| 2019/0060622 A1 | 2/2019 | Beeckler |
| 2019/0117301 A1 | 4/2019 | Steinke et al. |
| 2019/0143079 A1 | 5/2019 | Beeckler et al. |
| 2019/0175262 A1 | 6/2019 | Govari et al. |
| 2019/0175263 A1 | 6/2019 | Altmann et al. |
| 2019/0183567 A1 | 6/2019 | Govari et al. |
| 2019/0201669 A1 | 7/2019 | Govari et al. |
| 2019/0217065 A1 | 7/2019 | Govari et al. |
| 2019/0223948 A1 | 7/2019 | Stewart et al. |
| 2019/0297441 A1 | 9/2019 | Dehe et al. |
| 2019/0298441 A1 | 10/2019 | Clark et al. |
| 2019/0365451 A1 | 12/2019 | Jung, Jr. |
| 2020/0001054 A1 | 1/2020 | Jimenez et al. |
| 2020/0015693 A1 | 1/2020 | Beeckler et al. |
| 2020/0085497 A1 | 3/2020 | Zhang et al. |
| 2020/0155226 A1 | 5/2020 | Valls et al. |
| 2020/0163707 A1 | 5/2020 | Sliwa et al. |
| 2021/0169567 A1 | 6/2021 | Govari et al. |
| 2021/0290215 A1 | 9/2021 | Amanatullah et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |

(56)                    References Cited

FOREIGN PATENT DOCUMENTS

| CN | 104379212 | A | 2/2015 |
|---|---|---|---|
| CN | 104546117 | A | 4/2015 |
| CN | 105105844 | A | 12/2015 |
| CN | 105473091 | A | 4/2016 |
| CN | 105473093 | A | 4/2016 |
| CN | 106456247 | A | 2/2017 |
| CN | 109414286 | A | 3/2019 |
| CN | 111096788 | A | 5/2020 |
| EP | 0779059 | A1 | 6/1997 |
| EP | 1790304 | A2 | 5/2007 |
| EP | 2749214 | A1 | 7/2014 |
| EP | 2865350 | A2 | 4/2015 |
| EP | 2875790 | A2 | 5/2015 |
| EP | 2950734 | A2 | 12/2015 |
| EP | 3238646 | A2 | 11/2017 |
| EP | 3238648 | A1 | 11/2017 |
| EP | 3251622 | A1 | 12/2017 |
| EP | 3300680 | A1 | 4/2018 |
| EP | 3315087 | A1 | 5/2018 |
| EP | 3332727 | A2 | 6/2018 |
| EP | 3571983 | A2 | 11/2019 |
| EP | 3586778 | A1 | 1/2020 |
| EP | 3653153 | A1 | 5/2020 |
| JP | H06261951 | A | 9/1994 |
| JP | H1176233 | A | 3/1999 |
| JP | 2000504242 | A | 4/2000 |
| JP | 2005052424 | A | 3/2005 |
| JP | 2008515544 | A | 5/2008 |
| JP | 2010507404 | A | 3/2010 |
| JP | 2012024156 | A | 2/2012 |
| JP | 2013013726 | A | 1/2013 |
| JP | 2013078587 | A | 5/2013 |
| JP | 2013529109 | A | 7/2013 |
| JP | 2014529419 | A | 11/2014 |
| JP | 2015503365 | A | 2/2015 |
| JP | 2015100706 | A | 6/2015 |
| JP | 2015112113 | A | 6/2015 |
| JP | 2015112114 | A | 6/2015 |
| JP | 2015518776 | A | 7/2015 |
| JP | 2016515442 | A | 5/2016 |
| JP | 2016116863 | A | 6/2016 |
| JP | 2016527959 | A | 9/2016 |
| JP | 2016185296 | A | 10/2016 |
| JP | 2018108376 | A | 7/2018 |
| JP | 2018524085 | A | 8/2018 |
| JP | 2019515755 | A | 6/2019 |
| JP | 2019515756 | A | 6/2019 |
| JP | 2018515314 | A | 8/2023 |
| WO | 9605768 | A1 | 2/1996 |
| WO | 0056237 | A2 | 9/2000 |
| WO | 02102231 | A2 | 12/2002 |
| WO | 2005041748 | A2 | 5/2005 |
| WO | 2008049087 | A2 | 4/2008 |
| WO | 2011143468 | A2 | 11/2011 |
| WO | 2013049601 | A2 | 4/2013 |
| WO | 2013052919 | A2 | 4/2013 |
| WO | 2013154776 | A2 | 10/2013 |
| WO | 2014022379 | A1 | 2/2014 |
| WO | 2014168987 | A1 | 10/2014 |
| WO | 2015049784 | A1 | 4/2015 |
| WO | 2015200518 | A1 | 12/2015 |
| WO | 2016183337 | A2 | 11/2016 |
| WO | 2016210437 | A1 | 12/2016 |
| WO | 2017024306 | A1 | 2/2017 |
| WO | 2017087549 | A1 | 5/2017 |
| WO | 2018106569 | A1 | 6/2018 |
| WO | 2018129133 | A1 | 7/2018 |
| WO | 2019095020 | A1 | 5/2019 |
| WO | 2021119479 | A1 | 6/2021 |

OTHER PUBLICATIONS

Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.

Co-Pending U.S. Appl. No. 14/578,807, filed Dec. 22, 2014, 21 pages.

Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.

Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.

Extended European Search Report for Application No. EP17168513.4 mailed Sep. 18, 2017, 11 pages.

Extended European Search Report for European Application No. 15201723.2, mailed May 11, 2016, 07 Pages.

Extended European Search Report for European Application No. 17168393.1 mailed Dec. 15, 2017, 12 Pages.

Extended European Search Report for European Application No. 17168518.3, mailed Sep. 20, 2017, 9 Pages.

Extended European Search Report for European Application No. 17173893.3, mailed Nov. 6, 2017, 8 Pages.

Extended European Search Report for European Application No. 17201434.2, mailed Feb. 1, 2018, 10 Pages.

Extended European Search Report for European Application No. 17205876.0, mailed Jun. 1, 2018, 13 Pages.

Extended European Search Report for European Application No. 19177365.4, mailed Nov. 8, 2019, 07 Pages.

Extended European Search Report for European Application No. 19183327.6, mailed Nov. 21, 2019, 8 Pages.

Extended European Search Report for European Application No. 20153872.5, mailed May 7, 2020, 9 Pages.

Extended European Search Report for European Application No. 20195648.9, mailed Feb. 12, 2021, 8 Pages.

Extended European Search Report for European Application No. 21201890.7, mailed Jun. 14, 2022, 14 Pages.

Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.

Haines D.E., et al., "The Promise of Pulsed Field Ablation," Dec. 2019, vol. 19, No. 12, 10 pages.

Honarbakhsh S., et al., "Radiofrequency Balloon Catheter Ablation for Paroxysmal Atrial Fibrillation, Radiance Study—a UK experience," EP Europace, Oct. 2017, vol. 19, No. 1, p. i21, 3 Pages.

International Search Report and Written Opinion for International Application No. PCT/IB2019/052313, mailed Jul. 22, 2019, 8 Pages.

International Search Report and Written Opinion for International Application No. PCT/IB2019/056381, mailed Dec. 17, 2019, 10 pages.

International Search Report and Written Opinion for International Application No. PCT/IB2019/057743, mailed Dec. 6, 2019, 16 Pages.

International Search Report and Written Opinion issued in corresponding International Application No. PCT/IB2019/057742, dated Nov. 28, 2019, 18 Pages.

Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.

Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.

Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.

(56)　　　　　References Cited

OTHER PUBLICATIONS

Partial European Search Report for European Application No. 17168393.1 mailed Sep. 13, 2017, 13 Pages.
Partial European Search Report for European Application No. 17205876.0, mailed Feb. 22, 2018, 10 Pages.
Partial European Search Report for European Application No. 21201890.7, mailed Mar. 14, 2022, 15 Pages.
Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 Pages.
Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.
Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QkMWJME].
Youtube: "New Interface TactiCath Contact Force Ablation Catheter," Nov. 26, 2013, 1 Pages, [Retrieved on Nov. 19, 2020], Retrieved from URL: https: /Avww.youtube.com/watch?v=aYvYO8Hpylg].

Extended European Search Report for European Application No. 21191243.1, mailed Jan. 21, 2022, 6 Pages.
Notice of Reasons for Refusal dated Jan. 28, 2025, from corresponding Japanese Application No. 2021-131893.
Search Report dated Jan. 29, 2025, from corresponding Japanese Application No. 2021-131893.
Written Opinion with English translation dated Mar. 31, 2025, from corresponding Japanese Application No. 2021-131893.
Decision to Grant a Patent with English translation dated Jun. 3, 2025, from corresponding Japanese Application No. 2021-131893.
First Search dated Jul. 16, 2025, from corresponding Chinese Application No. CN202110934298.3.
First Office Action with English translation dated Jul. 16, 2025, from corresponding Chinese Application No. CN202110934298.3.
Supplementary Search dated Sep. 19, 2025, from corresponding Chinese Application No. 202110934298.3.
Second Office Action with English translation dated Sep. 19, 2025, from corresponding Chinese Application No. 202110934298.3.
Thomas Kueffer, et al, "Dose-dependent ventricular lesion formation using a novel large-area pulsed field ablation catheter: A preclinical feasibility study", Heart Rhythem Society 2025, pp. 1-9.

* cited by examiner

Receive a flexible PCB having electrical interconnections ⁓100

Dispose ablation electrode(s) on PCB and connect to interconnections ⁓102

Couple return electrode(s) to catheter shaft and/or within internal volume of inflatable balloon ⁓104

Wrap PCB around inflatable balloon and couple balloon to catheter shaft ⁓106

BALLOON CATHETER HAVING ABLATION AND RETURN ELECTRODES

FIELD OF THE INVENTION

The present invention relates generally to medical devices, and particularly to methods and systems for performing unipolar ablation procedures using a catheter having an expandable frame.

BACKGROUND OF THE INVENTION

Various types of diagnostic and therapeutic catheters, such as balloon catheters, may be used in mapping and/or treatment applications, such as in unipolar ablation of a patient organ.

For example, U.S. Patent Application Publication 2016/0199127 describes tools and methodologies for treating systemic nerve hyperactivity through splenic and/or carotid denervation. The invention discloses devices for performing ablation and protecting a patient from formation of embolisms, and well as an ablation unit for performing branching ablation.

U.S. Pat. No. 9,925,001 describes a renal nerve ablation device including an elongate tubular member having a distal region. An expandable member may be coupled to the distal region. One or more active electrodes may be coupled to the expandable member. One or more ground electrodes may be coupled to the expandable member. The one or more active electrodes and/or the one or more ground electrodes may be oriented helically about the length of the expandable member.

SUMMARY OF THE INVENTION

An embodiment of the present invention that is described herein provides a catheter including an expandable frame for insertion into an organ of a patient, one or more first electrodes, and a second electrode. The one or more first electrodes are disposed on the expandable frame at one or more first positions for placing in contact with a target tissue of the organ, and are configured to perform one or both of: (i) sensing one or more electrical signals from the target tissue, and (ii) applying one or more ablation pulses to the target tissue. The second electrode is disposed within an internal volume of the expandable frame, at a second position that is not in contact with the target tissue while the one or more first electrodes contact the target tissue, and is configured to serve as a return or common electrode for the electrical signals.

In some embodiments, the catheter includes an ablation power source, which is electrically connected to the catheter and is configured to apply one or more unipolar ablation pulses to the one or more first electrodes. In other embodiments, the organ includes a patient heart, and the one or more electrical signals include one or more unipolar intracardiac electrical signals sensed from the heart. In yet other embodiments, the organ includes a patient heart, and the one or more ablation pulses include one or more unipolar radiofrequency (RF) ablation pulses applied to the heart.

In an embodiment, the expandable frame includes an inflatable balloon. In another embodiment, the expandable frame includes an expandable basket.

There is additionally provided, in accordance with an embodiment of the present invention, a method for producing a catheter, the method including receiving an expandable frame for insertion into an organ of a patient. One or more first electrodes for placing in contact with a target tissue of the organ are disposed on the expandable frame, at one or more first positions. A second electrode, which serves as a return or common electrode for the electrical signals, is disposed within an internal volume of the expandable frame, at a second position that is not in contact with the target tissue while the one or more first electrodes contact the target tissue.

In some embodiments, disposing the one or more first electrodes includes producing the one or more first electrodes in the expandable frame. In other embodiments, disposing the second electrode includes coupling the second electrode to a catheter shaft at the second position, which is within the internal volume of the expandable frame.

In an embodiment, the method includes disposing at a third position that is not in contact with the target tissue while the one or more first electrodes contact the target tissue, a third electrode that serves as an additional return electrode for the electrical signals. In another embodiment, disposing the third electrode at the third position includes disposing the third electrode on a catheter shaft out of the internal volume of the expandable frame.

The present invention will be more fully understood from the following detailed description of the embodiments thereof, taken together with the drawings in which:

DETAILED DESCRIPTION OF EMBODIMENTS

Overview

Figure 1:
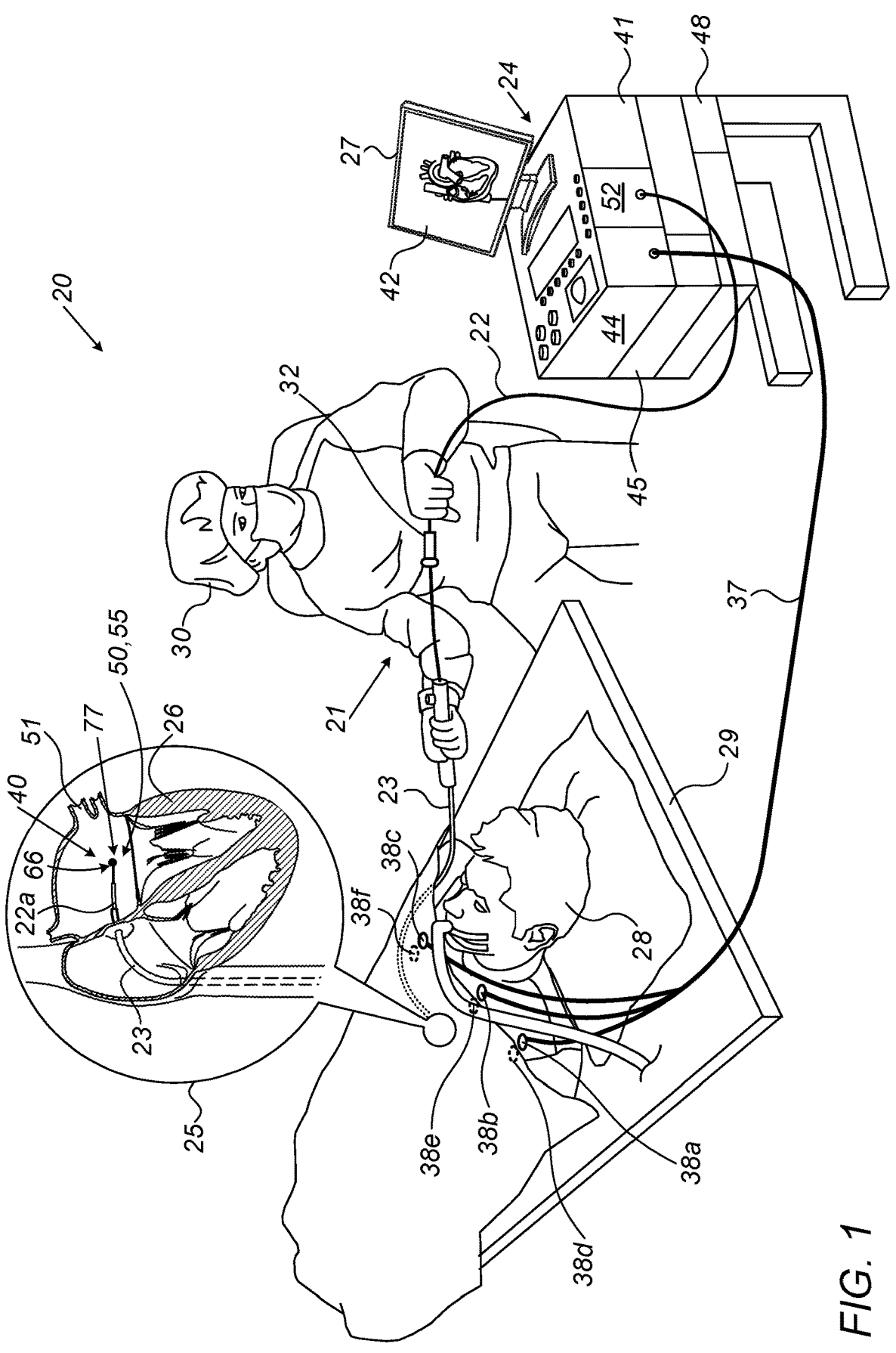
FIG. 1 is a schematic, pictorial illustration of a catheter-based position-tracking and radiofrequency (RF) ablation system, in accordance with an embodiment of the present invention.

Unipolar, also referred to as monopolar, radiofrequency (RF) ablation procedures are used in several medical applications, such as in sensing and ablation of a patient heart. In principle, a physician may acquire the unipolar signals and/or apply the unipolar pulses using one or more sensing/ablation electrodes together with a return electrode patch that may be coupled to the external patient skin. In this configuration, however, the large distance between the sensing/ablation electrode(s) in contact with the target tissue of patient heart, and the return electrode may (i) add noise to the unipolar signals acquired from the tissue, and/or (ii) have an increased impedance to the unipolar signals applied to the tissue during the RF ablation procedure.

An embodiment of the present invention that is described herein provides an ablation system having a catheter comprising an expandable frame, such as an expandable balloon or an expandable basket, coupled to a catheter tip at the catheter distal end, which is inserted into a patient heart.

In some embodiments, the catheter comprises one or more sensing and/or ablation electrodes, which are disposed on the expandable frame at one or more positions for placing in contact with a target tissue (intended to be ablated) of the heart, and are configured to perform one or both of: (i)

sensing one or more intra-cardiac electrical signals from the target tissue, and (ii) applying one or more RF ablation pulses to the target tissue.

In some embodiments, the catheter comprises an additional electrode, which is disposed within an internal volume of the expandable frame, at a position that is not in contact with the target tissue while the one or more sensing and/or ablation electrodes contact the target tissue. In such embodiments, the additional electrode is configured to serve as a return or common electrode for the electrical signals or the applied pulses, so as to: (i) enable acquisition of unipolar intra-cardiac electrical signals from the heart, and/or (ii) apply, using the ablation electrode(s), unipolar RF ablation pulses to the target tissue.

In some embodiments, the ablation system comprises a pulse generator, which is electrically connected to the catheter and is configured to apply the RF ablation pulses to the one or more ablation electrodes. The ablation system further comprises a processor, which is configured to receive the acquired intra-cardiac signals acquired by the sensing electrodes and to control the pulse generator to apply the RF ablation pulses to the ablation electrodes.

In some embodiments, the disclosed techniques may be used, mutatis mutandis, in other applications, such as in sensing and ablation procedures of renal nerves or sensing and/or ablation of other organs of a patient.

The disclosed techniques, and in particular the proximity between the sensing/ablation electrode and the return electrode that are disposed on the same catheter, reduce the noise level in electrical signals acquired from patient tissue, and improve accuracy of tissue ablation by having reduced impedance between the ablation electrode(s) and the return electrode used in the ablation procedure.

System Description

FIG. 1 is a schematic, pictorial illustration of a catheter-based position-tracking and radiofrequency (RF) ablation system 20, in accordance with an embodiment of the present invention.

Reference is now made to an inset 25. In some embodiments, system 20 comprises a catheter tip 40 that is fitted at a distal end 22a of a shaft 22 of a catheter 21 shown in the general view of FIG. 1.

In some embodiments, catheter tip 40 comprises an expandable frame, in the present example, an inflatable balloon 66 having multiple electrodes, such as but not limited to (i) multiple sensing and/or RF ablation electrodes 77, and (ii) one or more electrodes 50 and 55, configured to serve as a return or common electrode as will be described in detail below. In some embodiments, electrodes 77 and electrodes 50 and 55 are used as return electrodes for acquiring unipolar signals from an ostium 51 of a pulmonary vein (PV) in a heart 26, or for ablating one or more unipolar ablation pulses to ostium 51 in heart 26. Balloon 66 and electrodes 50, 55 and 77 are described in detail in FIG. 2 below.

Reference is now made back to the general view of FIG. 1. In some embodiments, the proximal end of catheter 21 is connected to a control console 24 comprising an RF generator 45 for applying the unipolar ablation pulses to tissue of ostium 51. An ablation protocol comprising ablation parameters is stored in a memory 48 of console 24.

In some embodiments, a physician 30 inserts distal end 22a of shaft 22 through a sheath 23 into heart 26 of a patient 28 lying on a table 29. Physician 30 advances the distal end of shaft 22 to ostium 51, also referred to herein as a target location, in heart 26 by manipulating shaft 22 using a manipulator 32 near the proximal end of catheter 21. During the insertion of distal end 22a, catheter tip 40 is maintained inside sheath 23 so as to minimize vascular trauma along the way to target location.

In some embodiments, system 20 comprises an impedance-based active current location (ACL) system, which may be used by physician 30 for navigating and tracking the position of catheter tip 30 in heart 26.

In an embodiment, physician 30 navigates the distal-end of shaft 22 to the target location by tracking the position of catheter tip 40. During navigation of distal end 22a in heart 26, console 24 receives signals from a coil (not shown) or from any other element, e.g., any of electrodes 50 and 55, which is configured to serve as an impedance-based position sensor of the ACL system.

In some embodiments, the ACL system comprises a plurality of electrodes 38, which are coupled to the body of patient 28, e.g., via patches 29 that adhere to the skin of patient 28. In the example of FIG. 1, system 10 comprises six electrodes, of which electrodes 38a, 38b, and 38c are coupled to the front (e.g., chest) of patient 28, and electrodes 38d, 38e, and 38f are coupled to the back of patient 28. As shown in FIG. 1, the electrodes are arranged in pairs as follows: electrodes 38a and 38d are facing one another at the right side of patient 28, electrodes 38c and 38f are facing one another at the left side of patient 28, and electrodes 38b and 38e are facing one another at the upper part of the chest and back of patient 28.

In other embodiments, system 20 may comprise any suitable number of electrodes, coupled to the patient skin in any suitable arrangement.

In some embodiments, electrodes 38a-38f are typically connected, via a cable 37, to a processor 41 of system 20, which is configured to receive from electrodes 38a-38f electrical signals indicative of the measured impedance, and, based on the received signals, to estimate the position of catheter tip 40 within heart 26 using techniques described herein.

In some embodiments, electrodes 38a-38f are typically used for navigating catheter 21 within the body of patient 28, using the aforementioned impedance-based ACL system and tracking techniques, such as those described, for example, in U.S. Pat. No. 8,456,182 and US Patent Application Publication 2015/0141798, whose disclosures are incorporated herein by reference.

In some embodiments, the ACL system is configured to estimate the position of catheter tip 40 responsively to the different impedances measured between the electrode(s) coupled to catheter tip 40, and each of electrodes 38a-38f.

In some embodiments, processor 41 is configured to estimate the position of catheter tip 40 in heart 26, and to display on a display 27 of console 24, a marker (not shown) overlaid on an anatomical image 42 (or a synthetic model) of heart 26. Physician 30 may use the marker, e.g., for navigating catheter tip 40 into ostium 51.

In some embodiments, once distal end 22a of shaft 22 has reached heart 26, physician 30 retracts sheath 23 and further manipulates shaft 22 to navigate catheter tip 40 to ostium 51 of the pulmonary vein, or to any other target location of heart 26.

In some embodiments, while catheter tip 40 is placed in contact with the tissue, physician 30 may control system 20 for acquiring unipolar intra-cardiac electrical signals from the target tissue of heart 26, and/or for applying unipolar ablation pulses to the target tissue.

In principle, physician 30 may acquire the unipolar signals using a return electrode (also referred to herein as an indifferent electrode or a neutral electrode) patch that is coupled externally to the skin of patient 28. Similarly, physician 30 may use the return electrode for applying the one or more unipolar ablation pulses to the tissue of heart 26. The return electrode may be selected from any of electrodes 38a-38f, or from an electrode patch used in any other configuration of electrodes, such as Wilson Central Terminal (WCT). Based on this configuration, physician 30 may control RF generator 45 to apply pulses of RF electric currents to be passed between electrodes 77 of catheter tip 40 and the selected indifferent electrode patch that is coupled externally to the skin of patient 28. In this configuration, however, the large distance between electrodes 77 (in contact with the target tissue of heart 26) and the selected indifferent electrode may (i) add noise to the unipolar signals acquired from the tissue, and/or (ii) increased impedance to the unipolar signals applied to the tissue during the RF ablation procedure.

Techniques to overcome the added noise and/or the increased impedance are described in detail in FIG. 2 below.

Processor 41 is typically a general-purpose computer, with suitable front end and (a) ECG interface circuits 44 for receiving ECG signals from electrodes 38, and (b) an electrical interface circuit 52 for receiving signals from catheter 21, as well as for applying RF energy treatment via catheter 21 in a left atrium of heart 26 and for controlling the other components of system 20. Processor 41 typically comprises a software in a memory 48 of system 20 that is programmed to carry out the functions described herein. The software may be downloaded to the computer in electronic form, over a network, for example, or it may, alternatively or additionally, be provided and/or stored on non-transitory tangible media, such as magnetic, optical, or electronic memory.

This particular configuration of system 20 is shown by way of example, in order to illustrate certain problems that are addressed by embodiments of the present invention and to demonstrate the application of these embodiments in enhancing the performance of such an ablation system. Embodiments of the present invention, however, are by no means limited to this specific sort of example system, and the principles described herein may similarly be applied to other sorts of ablation systems.

In other embodiments, instead of balloon 66, catheter tip 40 may have any other suitable component, such as an expandable basket or any other suitable type of an expandable frame.

Figures 2, 3:
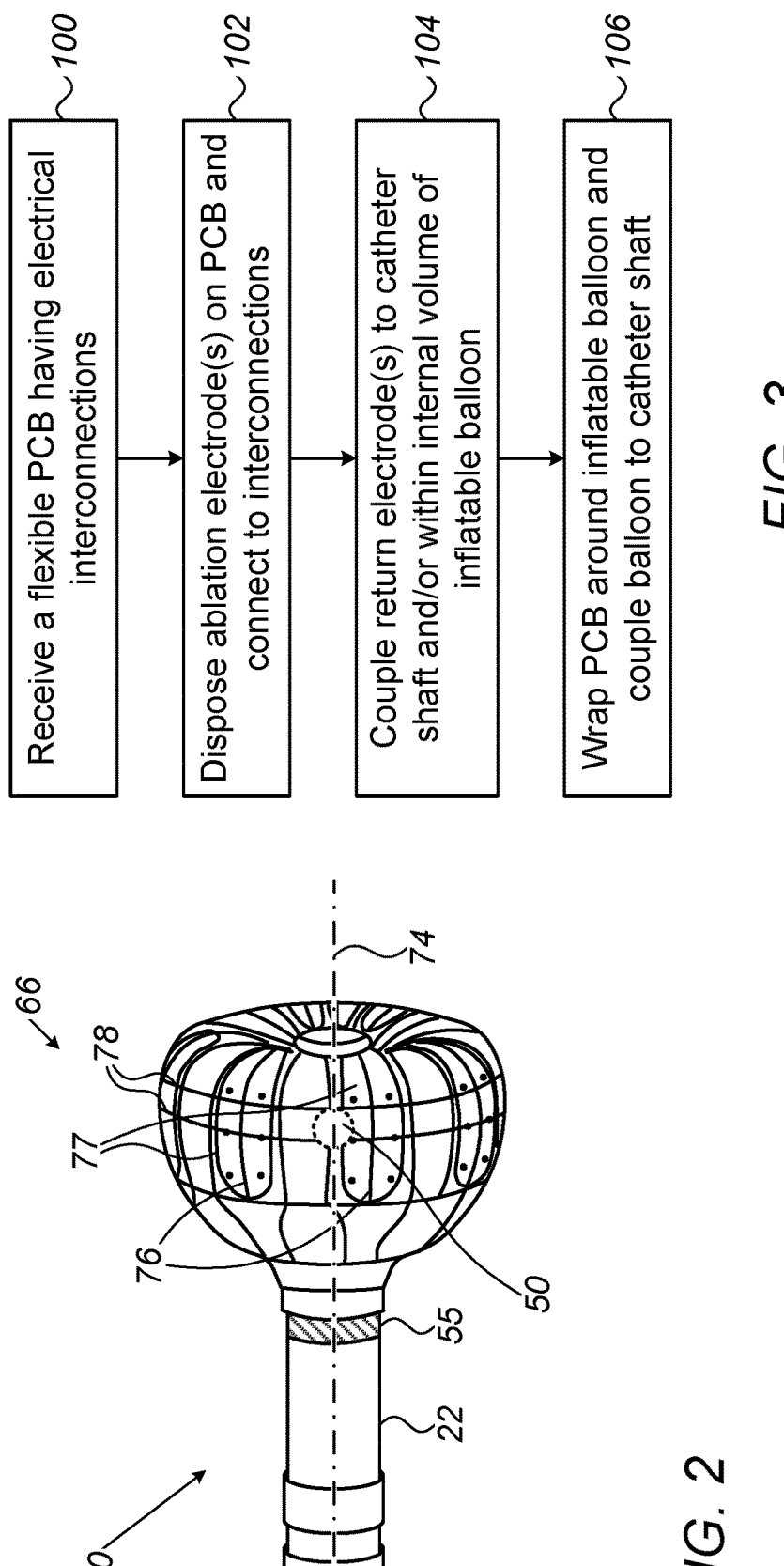
FIG. 2 is a schematic, pictorial illustration of a catheter tip of the RF ablation system, in accordance with an embodiment of the invention.
FIG. 3 is a flow chart that schematically illustrates a method for producing a catheter tip comprising a balloon and multiple electrodes, in accordance with an embodiment of the invention.

Performing Unipolar Ablation Using a Return
Electrode Integrated in Ablation Balloon Catheter FIG. 2 is a schematic, pictorial illustration of catheter tip 40, in accordance with an embodiment of the invention.

In some embodiments, balloon 66 or any other expandable frame that is coupled to catheter tip 40 of catheter 21, is typically in a collapsed position when physician 30 moves catheter tip 40 to the target location, and is configured to be expanded at the target location.

In the context of the present disclosure, the expandable frame has a collapsed position and an expanded position, and specifically, balloon 66 has a collapsed position and an inflated position, which corresponds to the expanded position of the expandable frame. Note that the description below refers to balloon 66, but the techniques described below may be applied, mutatis mutandis, to any catheter having other sorts of expandable frames, such as but not limited to a basket catheter.

In some embodiments, balloon 66 has a diameter of about 12 mm, or any other suitable diameter, and comprising electrodes 77 disposed on the surface of balloon 66. In some embodiments, when placed in contact with tissue of heart 26, electrodes 77 are configured to sense intra-cardiac electrical signals from the tissue. In the example of FIG. 2, balloon 66 has multiple electrodes 77 so as to obtain high-resolution mapping of the electrical signals in tissue. In the present example, catheter tip 40 is configured to acquire from the tissue unipolar intra-cardiac electrical signals.

In the context of the present disclosure and in the claims, the terms "about" or "approximately" for any numerical values or ranges indicate a suitable dimensional tolerance that allows the part or collection of components to function for its intended purpose as described herein.

In some embodiments, electrodes 77 are further configured to apply to the tissue, one or more unipolar RF ablation pulses received from RF generator 45 and controlled by processor 41 and/or by physician 30, as described in FIG. 1 above. In some embodiments, by using one electrode 77 in contact with the tissue, physician 30 may obtain high-resolution ablation (e.g., form a narrow lesion) at a desired locations of the ablated tissue.

In some embodiments, physician 30 may determine the depth of lesion by controlling, inter alia, the energy and duration of RF ablation pulses applied to the tissue at the target location.

In some embodiments, catheter tip 40 comprises electrode 55, which is coupled to shaft 22 at a selected proximity to balloon 66, and is configured to serve as a return electrode. Note that when balloon 66 is in an inflated position, one or more electrodes 77 are placed in contact with the target tissue (e.g., of ostium 51), but electrode 55 is placed in contact with the blood pool of heart 26 but not directly with the target tissue. Therefore, electrode 55 can serve as a return electrode for sensing unipolar signals from the target tissue and/or for applying unipolar ablation pulses to the target tissue.

In some embodiments, catheter tip 40 may comprise electrode 50, which is disposed within the internal volume of balloon 66 and is therefore shown in FIG. 2 as a dashed element, at a position that is not placed in contact with the target tissue. For example, electrode 50 may be coupled to shaft 22 along an axis 74 of catheter tip 40. In this configuration, when balloon 66 is in an inflated position, one or more electrodes 77 are placed in contact with the target tissue. Electrode 50, however, is within the internal volume of balloon 66, and therefore, is not placed in contact with the target tissue, but with another tissue (e.g., the blood pool of heart 26) or with a saline solution used for inflating balloon 66. Note that both the blood and the saline solution are electrically conductive, and therefore, are configured to conduct the sensed signals and/or the applied pulses described above, so that electrode 50, as well as electrode 55, may serve as a return or common electrode as described above. Moreover, in case electrode 50 or 55 makes contact with the target tissue together with one or more electrodes 77, the aforementioned sensed signals and or applied pulses may be bipolar, e.g., between electrodes 77 and 50 or between electrodes 77 and 55, which is undesired and, in some cases, may cause damage to heart 26.

In some embodiments, balloon 66 may comprise a flexible substrate, such as but not limited to a flexible printed circuit board (PCB), having printed electrical interconnections. In the present example, the electrical interconnections comprise electrical traces 76, which are parallel to axis 74 of catheter tip 40, and electrical traces 78, which are orthogonal to axis 74. The flexible PCB is wrapped around the surface of balloon 66, so that electrical traces 76 and 78 are configured to conduct electrical signals and/or RF ablation pulses between electrode 77 and console 24.

The configuration of balloon 66 is provided by way of example, in order to illustrate certain problems that are addressed by embodiments of the present invention and to demonstrate the application of these embodiments in enhancing the performance of a catheter tip of such an ablation catheter. Embodiments of the present invention, however, are by no means limited to this specific sort of example catheter tip, and the principles described herein may similarly be applied to other sorts of ablation catheters.

In other embodiments, instead of balloon 66, catheter tip 40 may have any other suitable component, such as a basket-type distal end having an expandable frame, which is coupled to shaft 22 of catheter 21. In such embodiments, electrodes 77 may be coupled to splines of the expandable frame of the basket, and electrode 50 may be coupled to shaft 22 within the internal volume of the expandable frame. Additionally or alternatively, electrode 55 may be coupled to shaft 22, e.g., at the position shown in FIG. 2. Note that electrodes 50 and 55 are configured to serve as return or common electrodes for the electrical signals sensed by electrodes 77, therefore, catheter tip 40 may comprise only one of electrodes 50 and 55. In this configuration, electrode 50 or electrode 55 is in contact with the blood pool of heart 26 and is not placed in contact with the target tissue of heart 26.

Producing Ablation Balloon Catheter Having a Return Electrode

FIG. 3 is a flow chart that schematically illustrates a method for producing catheter tip 40, in accordance with an embodiment of the invention. The method begins at a substrate receiving step 100 with receiving the flexible PCB having electrical interconnections, such as electrical traces 76 and 78. At an ablation electrodes disposing step 102, one or more ablation electrode(s) 77 are disposed on the flexible PCB and connected to electrical traces 76 and 78. In the context of the present disclosure and in the claims, the term "dispose" refers to "form" or "produce" (electrodes 77 in the PCB, e.g., using any suitable PCB production process) or to "couple" or "attach" (electrodes 77 to the PCB, using any suitable coupling technique, such as but not limited to soldering).

At a return electrode coupling step 104, one or more return electrodes 50 and 55, but typically one return electrode is sufficient, is coupled to catheter tip 40 at distal end 22a of catheter 21. Note that the position of electrodes 50 and 55 is provided by way of example, so as to shown that, when balloon 66 or any other suitable type expandable frame is in an inflated or expanded position, one or more electrodes 77 are placed in contact with the target tissue, but neither electrode 50 nor electrode 55 is placed in contact with the target tissue. In other embodiments, a return or common electrode may be coupled to or produced in the expandable frame (e.g., balloon 66 or the aforementioned basket) at any suitable position, so that the return or common electrode does not make contact with the target tissue, when electrodes 77 are placed in contact with the target tissue for sensing the intra-cardiac electrical signals or for applying the one or more ablation pulses to the target tissue, as described in detail in FIGS. 1 and 2 above.

At a catheter tip assembling step 106 that concludes the method, the flexible PCB is wrapped around and coupled to balloon 66 (e.g., using bonding or soldering), and balloon 66 is coupled to distal end 22a of shaft 22 so as to complete the formation of catheter tip 40. Note that in case of using the aforementioned basket instead of balloon 66, step 106 may comprise coupling the basket to distal end 22a of shaft 22 so as to complete the production of catheter tip 40.

The configuration of catheter tip 40 and the production method thereof are simplified and described for the sake of conceptual clarity so as to show the key features of the disclosed invention.

Although the embodiments described herein mainly address unipolar sensing and ablation of cardiac tissue, the methods and systems described herein can also be used in other applications, such as in performing unipolar sensing and/or ablation in any other tissue of the patient body.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A catheter, comprising:

an expandable frame for insertion into an organ of a patient, the expandable frame extending along an axis of the catheter and comprising an inflatable balloon that is inflatable with a saline solution;

a flexible printed circuit board wrapped around the inflatable balloon and comprising first electrical traces that are parallel to the axis and second electrical traces that are orthogonal to the first electrical traces and extend in a circumferential direction of the inflatable balloon, the circumferential direction being orthogonal to and extending around the axis;

a plurality of first electrodes, which (i) are disposed on the flexible printed circuit board at a plurality of first positions along the circumferential direction of the inflatable balloon, (ii) are each configured to be in contact with a target tissue of the organ, and (iii) are each configured to perform one or both of: (i) sensing one or more unipolar electrical signals from the target tissue, and (ii) applying one or more unipolar ablation pulses to the target tissue, each second electrical trace (i) extending across at least three first electrodes of the plurality of first electrodes and (ii) intersecting the plurality of first electrical traces in the circumferential direction; and a second electrode, which is disposed within an internal volume of the expandable frame, at a second position that is not in contact with the target tissue while the plurality of first electrodes contact the target tissue, and is configured to serve as a return or common electrode to sense the one or more unipolar electrical signals from the target tissue or apply the one or more unipolar ablation pulses to the target tissue, the second electrode being disposed within the inflatable balloon, and the saline solution being configured to conduct one or both of: (i) the one or more unipolar electrical signals sensed from the target tissue, and (ii) the one or more unipolar ablation pulses applied to the target tissue.

2. The catheter according to claim 1, and comprising an ablation power source, which is electrically connected to the catheter and is configured to apply the one or more unipolar ablation pulses to at least one first electrode of the plurality of first electrodes.

3. The catheter according to claim 1, wherein the organ comprises a patient heart, and wherein the one or more unipolar electrical signals comprise one or more unipolar intra-cardiac electrical signals sensed from the organ.

4. The catheter according to claim 1, wherein the organ comprises a patient heart, and wherein the one or more unipolar ablation pulses comprise one or more unipolar radiofrequency (RF) ablation pulses applied to the patient heart.

5. The catheter according to claim 1, wherein the second electrode is coupled to a catheter shaft at the second position.

6. The catheter according to claim 1, further comprising a third electrode at a third position that is not in contact with the target tissue while the plurality of first electrodes contact the target tissue, the third electrode serving as an additional return electrode for the one or more unipolar electrical signals.

7. The catheter according to claim 6, wherein the third electrode is disposed on a catheter shaft out of the internal volume of the inflatable balloon.

8. The catheter according to claim 1, each respective first electrical trace extending along a respective first electrode of the plurality of first electrodes such that the respective first electrode comprises portions disposed on opposing lateral sides of the respective first electrical trace in the circumferential direction.

9. A method for producing a catheter, the method comprising:

receiving an expandable frame for insertion into an organ of a patient, the expandable frame extending along an axis and comprising an inflatable balloon that is inflatable with a saline solution;

receiving a flexible printed circuit board that comprises first electrical traces and second electrical traces;

disposing on the flexible printed circuit board, at a plurality of first positions along a circumferential direction of the inflatable balloon, a plurality of first electrodes for placing in contact with a target tissue of the organ, each of the plurality of first electrodes performing one or both of: (i) sensing one or more unipolar electrical signals from the target tissue, and (ii) applying one or more unipolar ablation pulses to the target tissue;

wrapping the flexible printed circuit board around the inflatable balloon such that the first electrical traces are parallel to the axis and the second electrical traces that are orthogonal to the first electrical traces and extend in the circumferential direction, the circumferential direction being orthogonal to and extending around the axis when the flexible printed circuit board is wrapped around the inflatable balloon, each second electrical trace (i) extending across at least three first electrodes of the plurality of first electrodes and (ii) intersecting the plurality of first electrical traces in the circumferential direction, and each respective first electrical trace extending along a respective first electrode of the plurality of first electrodes such that the respective first electrode comprises portions disposed on opposing lateral sides of the respective first electrical trace in the circumferential direction; and disposing within an internal volume of the expandable frame, at a second position that is not in contact with the target tissue while the one or more first electrodes contact the target tissue, a second electrode that serves as a return or common electrode to sense the one or more unipolar electrical signals from the target tissue or apply the one or more unipolar ablation pulses to the target tissue, the second electrode being disposed within the inflatable balloon, and the saline solution being configured to conduct one or both of: (i) the one or more unipolar electrical signals sensed from the target tissue, and (ii) the one or more unipolar ablation pulses applied to the target tissue.

10. The method according to claim 9, and comprising electrically connecting to the catheter, an ablation power source for applying the one or more unipolar ablation pulses to at least one of the first electrodes of the plurality of first electrodes.

11. The method according to claim 9, wherein disposing the plurality of first electrodes comprises coupling the plurality of first electrodes to the expandable frame.

12. The method according to claim 9, wherein disposing the plurality of first electrodes comprises producing the plurality of first electrodes in the expandable frame.

13. The method according to claim 9, wherein disposing the second electrode comprises coupling the second electrode to a catheter shaft at the second position, which is within the internal volume of the expandable frame.

14. The method according to claim 9, and comprising disposing at a third position that is not in contact with the target tissue while the plurality of first electrodes contact the target tissue, a third electrode that serves as an additional return electrode for the one or more unipolar electrical signals.

15. The method according to claim 14, wherein disposing the third electrode at the third position comprises disposing the third electrode on a catheter shaft out of the internal volume of the expandable frame.

16. A catheter, comprising:

an expandable frame for insertion into an organ of a patient, the expandable frame comprising a flexible substrate wrapped around the expandable frame and an axis, the flexible substrate comprising first electrical traces that are parallel to the axis and second electrical traces that are orthogonal to the first electrical traces and extend in a circumferential direction of the expandable frame, the circumferential direction being orthogonal to and extending around the axis;

a plurality of first electrodes, which (i) are disposed on the flexible substrate at a plurality of first positions along the circumferential direction of the flexible substrate, (ii) are each configured to be in contact with a target tissue of the organ, and (iii) are each configured to perform one or both of: (i) sensing one or more unipolar electrical signals from the target tissue, and (ii) applying one or more unipolar ablation pulses to the target tissue, each second electrical trace (i) extending across at least three first electrodes of the plurality of first electrodes and (ii) intersecting the plurality of first electrical traces in the circumferential direction; and a second electrode, which is disposed within an internal volume of the expandable frame, at a second position that is not in contact with the target tissue while the plurality of first electrodes contact the target tissue, and is configured to serve as a return or common electrode to sense the one or more unipolar electrical signals from the target tissue or apply the one or more unipolar ablation pulses to the target tissue.

17. The catheter according to claim 16, each respective first electrical trace extending along a respective first electrode of the plurality of first electrodes such that the respective first electrode comprises portions disposed on opposing lateral sides of the respective first electrical trace in the circumferential direction.

* * * * *